United States Patent
Fukuda et al.

(10) Patent No.: US 8,138,368 B2
(45) Date of Patent: Mar. 20, 2012

(54) PROCESS FOR PRODUCING ACRYLONITRILE COMPOUND

(75) Inventors: Kenzo Fukuda, Sanyo Onoda (JP); Yasuo Kondo, Sanyo Onoda (JP); Norio Tanaka, Funabashi (JP); Hideaki Suzuki, Funabashi (JP); Masatoshi Ohnari, Chiyoda-ku (JP); Koichi Nishio, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 86 days.

(21) Appl. No.: 12/588,251

(22) Filed: Oct. 8, 2009

(65) Prior Publication Data
US 2010/0029951 A1   Feb. 4, 2010

Related U.S. Application Data

(62) Division of application No. 10/551,041, filed as application No. PCT/JP2004/004345 on Mar. 26, 2004, now Pat. No. 7,649,104.

(30) Foreign Application Priority Data

Mar. 28, 2003 (JP) ................. 2003-092029

(51) Int. Cl.
C07C 255/03 (2006.01)
C07C 211/78 (2006.01)
(52) U.S. Cl. ................. 558/441; 546/286
(58) Field of Classification Search ............ 558/441; 546/286
See application file for complete search history.

(56) References Cited

U.S. PATENT DOCUMENTS

| 6,187,944 | B1 | 2/2001 | Koyanagi et al. |
| 6,492,404 | B1 * | 12/2002 | Shibata et al. ........... 514/365 |

FOREIGN PATENT DOCUMENTS

| JP | A 59-110691 | 6/1984 |
| JP | A 2000-290279 | 10/2000 |
| WO | WO 97/40009 A1 | 10/1997 |
| WO | WO 98/35935 A1 | 8/1998 |
| WO | WO 98/42683 A1 | 10/1998 |
| WO | WO 99/44993 A1 | 9/1999 |
| WO | WO 01/07410 A1 | 2/2001 |
| WO | WO 01/09086 A1 | 2/2001 |
| WO | WO 01/29003 A1 | 4/2001 |
| WO | WO 01/68589 A1 | 9/2001 |

OTHER PUBLICATIONS

Kayaleh, N. et al., "Enolate Ions as β-Activators of Ortho-Metalation: Direct Synthesis of 3-Aminoindenones," J. Org. Chem., vol. 65, pp. 4515-4522, 2000.

Kayaleh, N. et al., "A New Anionic Cyclization Reaction: Condensation of Benzoate Esters with Nitriles to Give 3-Amino-2-Inden-1-Ones," Tetrahedron Letters, vol. 38, No. 47, pp. 8121-8124, 1997.

Haddow, J. et al., "Latent Inhibitors. Part 5.[1,†] Latent Inhibition of Dihydrofolate Reductase by a Pteridine-spiro-cyclopropane," J. Chem. Soc. Perkin Trans. I, pp. 1297-1304, 1989.

Bunting, J. et al., "Equilibrium and Kinetic Acidities of Benzylic Ketones, Application of the Marcus Equation to the Deprotonation of Carbon Acids," J. Am. Chem. Soc, vol. 110, pp. 4008-4017, 1988.

Sakamoto, T. et al. "Studies on Pyrimidine Derivatives. XXVI.[1]) Synthesis of Derivatives containing a 1,3-Dicarbonyl Side Chain," Chem. Pharm. Bull. 30(3), pp. 1033-1035, 1982.

* cited by examiner

Primary Examiner — James O Wilson
Assistant Examiner — Ebenezer O Sackey
(74) Attorney, Agent, or Firm — Oliff & Berridge, PLC

(57) ABSTRACT

There is provided a process for stereoselectively producing E-form of 3-acyloxyacrylonitrile compound (3) or Z-form which comprises reacting 3-oxopropionitrile compound (1) with an acid chloride (2), characterized in that the reaction is conducted with removal of hydrogen chloride, or by using an organic base or an inorganic base, to thereby regulate the stereostructure of the product; a process for producing the compound (1) characterized by reacting acetonitrile compound (5) with an aromatic ester compound (6) by use of an alkali metal alkoxide in a hydrocarbon solvent while removing alcohol formed as a by-product by azeotropic distillation in a separating tank; and a process for isomerizing E-form of 3-acyloxyacrylonitrile compound to Z-form thereof by use of an organic base.

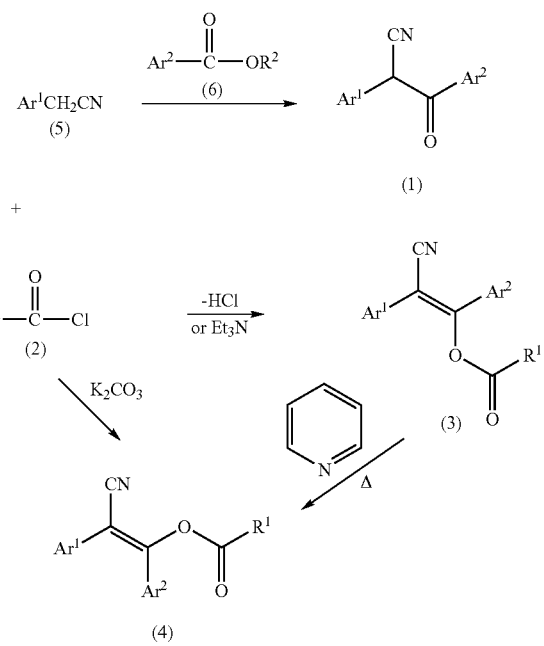

12 Claims, No Drawings

PROCESS FOR PRODUCING ACRYLONITRILE COMPOUND

This is a Division of application Ser. No. 10/551,041 filed Sep. 27, 2005, which in turn is a National Stage of Application No. PCT/JP2004/04345, filed Mar. 26, 2004, which claims priority to Japanese Patent Application No. 2003-092029, filed Mar. 28, 2003. The disclosure of the prior applications are hereby incorporated by reference herein in their entirety.

TECHNICAL FIELD

The present invention relates to an industrial process for producing 3-acyloxyacrylonitrile compound as an agricultural and horticultural pesticide described in International Patent Publication WO97/40009 pamphlet, and an industrial process for producing 3-oxopropionitrile compound that is the intermediate thereof and useful as several fine chemical intermediates represented by physiologically active substances such as pharmaceuticals and agrochemical, etc.

BACKGROUND ART

As processes for producing 3-acyloxyacrylonitrile compound, the followings are known.

There is an example in which 3-oxopropionitrile compound is reacted with an acid chloride to obtain 3-acyloxyacrylonitrile compound. However, the resulting product is a mixture of E- and Z-stereoisomers, and there is no document in which only either isomer is obtained in a high yield (see, for example Patent Documents 1, 2 and 3).

Although there is a document in which either isomer can be produced by reacting 3-oxopropionitrile compound with an acid chloride, chloro formic acid derivative is merely used as an example and there is no example in which a carboxylic chloride is used (see, for example Patent Document 4).

The process for producing 3-oxopropionitrile compound in which an acetonitrile compound is reacted with an aromatic ester compound is industrially more advantageous than the process for producing 3-oxopropionitrile compound in which an acetonitrile compound is reacted with an aromatic acid chloride.

That is, the advantages are to obviate two steps of hydrolyzing an aromatic ester compound and converting to an aromatic acid chloride, and to be able to reduce the amount of base used by one equivalent compared to the reaction by use of an aromatic acid chloride.

At present, as the process for producing 3-oxopropionitrile compound in which an acetonitrile compound is reacted with an aromatic ester compound, the followings are known.

Non-patent Documents 1 and 2 disclose a production process by use of sodium hydride or lithium/diisopropyl amide in THF solvent. However, a base used is expensive and further dangerous in handling it in an industrial production.

Although Non-patent Documents 3 and 4 and Patent Document 5 disclose a production process by use of sodium ethoxide in ethanol solvent, it occurs a large amount of by-product and thus has a low yield.

Although Patent Document 4 discloses an example in which solid sodium ethoxide is used in toluene solvent, it has a low yield. In addition, Non-patent Document 5 and Patent Documents 6 and 7 disclose processes in which methanol solution of sodium methoxide in toluene solvent or solid sodium methoxide is used and methanol as a by-product is temporarily or continuously distilled off after the reaction or during the reaction. However, the yield of these processes is 38 to 76% and is not so high. Although the yield is improved by removing methanol as a by-product, as the solvent is distilled off together, there are disadvantages that in an industrial scale, it is required to distil off while adding the solvent and therefore procedure becomes tedious, and that a large amount of the solvent is required.

Further, there is a process disclosed in Patent Document 8 in which magnesium alkoxide is used. However, the magnesium alkoxide is expensive, is no universal reagent and is not industrially used.

In addition, as a process in which E-3-acyloxyacrylonitrile compound or a mixture thereof with Z-3-acyloxyacrylonitrile compound is isomerized to obtain Z-3-acyloxyacrylonitrile compound, a process by use of isomerization with light is disclosed (see, for example Patent Document 4). However, a process for obtaining pure Z-3-acyloxyacrylonirile compound by isomerization with an organic base by making use of difference in solubility between E-form and Z-form is not known.

Patent Document 1: International Patent Publication WO97/40009 pamphlet

Patent Document 2: International Patent Publication WO98/35935 pamphlet

Patent Document 3: International Patent Publication WO99/44993 pamphlet

Patent Document 4: International Patent Publication WO01/09086 pamphlet

Patent Document 5: JP 59-110691 A

Patent Document 6: International Patent Publication WO01/29003 pamphlet

Patent Document 7: International Patent Publication WO01/07410 pamphlet

Patent Document 8: International Patent Publication WO01/68589 pamphlet

Non-patent Document 1: J. Org. Chem., 65, 4515 (2000)

Non-patent Document 2: Tetrahedron Lett., 38, 9121 (1997)

Non-patent Document 3: J. Chem. Soc. Perkin trans. I, 1297 (1989)

Non-patent Document 4: J. Am. Chem. Soc., 110, 4008 (110)

Non-patent Document 5: Chem. Pharm. Bull., 30, 1033 (1982)

DISCLOSURE OF THE INVENTION

The problem to be solved by the invention is to provide a process for producing 3-acyloxyacrylonitrile compound and 3-oxopropionitrile compound that is industrially advantageous.

The present inventors eagerly investigated in order to solve the above-mentioned problem. As a result of it, they found a process in which E- or Z-form of 3-acyloxyacrylonitrile compound can be produced in a stereoselective manner by a reaction between 3-oxopropionitrile compound and an acid chloride, and further found a process for producing 3-oxopropionitrile compound being an intermediate thereof, which is industrially inexpensive and universal and has a high yield, by comprising reacting an acetonitrile compound with an aromatic ester compound by use of an alkali metal alkoxide in a aliphatic hydrocarbon solvent, optionally while alcohol as a by-product is azeotropically distilled off at the presence of a polar solvent, and they completed the present invention.

That is, the present invention relates to the following [1] to [16]:

[1] A process for stereoselectively producing E-3-acyloxyacrylonitrile compound of formula (3)

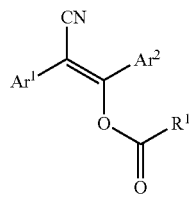
(3)

wherein $Ar^1$ and $Ar^2$ are independently of each other an aromatic substituent that may be substituted, and $R^1$ is an alkyl group that may be substituted, or an aromatic substituent that may be substituted, or Z-3-acyloxyacrylonitrile compound of formula (4)

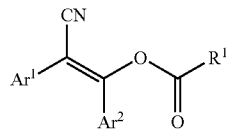
(4)

wherein $Ar^1$, $Ar^2$ and $R^1$ have meaning similar to the above, which comprises reacting 3-oxopropionitrile compound of formula (1)

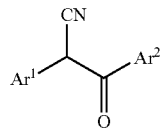
(1)

wherein $Ar^1$ and $Ar^2$ have meaning similar to the above, with an acid chloride of formula (2)

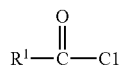
(2)

wherein $R^1$ has meaning similar to the above, characterized in that
the reaction is conducted with removal of hydrogen chloride as a by-product from the system without using a base, or by using an organic base as a base or an inorganic base of alkali metal or alkaline earth metal as a base, to thereby regulate stereostructure of reaction product.

[2] The process for stereoselectively producing E-3-acyloxyacrylonitrile compound as set forth in [1], characterized in that the reaction of the 3-oxopropionitrile compound of formula (1) with the acid chloride of formula (2) is conducted with removal of hydrogen chloride as a by-product from the system without using a base.

[3] The process for stereoselectively producing E-3-acyloxyacrylonitrile compound as set forth in [1], characterized in that the reaction of the 3-oxopropionitrile compound of formula (1) with the acid chloride of formula (2) is conducted by using an organic base as a base.

[4] The process for stereoselectively producing Z-3-acyloxyacrylonitrile compound as set forth in [1], characterized in that the reaction of the 3-oxopropionitrile compound of formula (1) with the acid chloride of formula (2) is conducted by using an inorganic base of alkali metal or alkaline earth metal.

[5] The process as set forth in [1], [2], [3] or [4], wherein is used 3-oxopropionitrile compound of formula (1) wherein $Ar^1$ and $Ar^2$ have meaning similar

(5)

to the above, which is produced by reacting an acetonitrile compound of formula (5) wherein $Ar^1$ has meaning similar to the above, with an aromatic ester compound of

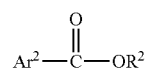
(6)

formula (6)
wherein $Ar^2$ has meaning similar to the above, and $R^2$ is an alkyl group that may be substituted, by use of alkali metal alkoxide in an aliphatic hydrocarbon solvent, while removing alcohol as a by-product by azeotropic distillation in a separating tank.

[6] The process as set forth in [1], [2], [3] or [4], wherein is used 3-oxopropionitrile compound of formula (1) wherein $Ar^1$ and $Ar^2$ have meaning similar to the above, which is produced by reacting the acetonitrile compound of formula (5) with the aromatic ester compound of formula (6) by use of alkali metal alkoxide in an aliphatic hydrocarbon solvent, while removing alcohol as a by-product by azeotropic distillation in the presence of a polar solvent in a separating tank.

[7] A process for producing 3-oxopropionitrile compound of formula (1) characterized by reacting the acetonitrile compound of formula (5) with the aromatic ester compound of formula (6) by use of an alkali metal alkoxide in an aliphatic hydrocarbon solvent, while removing alcohol as a by-product by azeotropic distillation in a separating tank.

[8] A process for producing 3-oxopropionitrile compound of formula (1) characterized by reacting the acetonitrile compound of formula (5) with the aromatic ester compound of formula (6) by use of an alkali metal alkoxide in an aliphatic hydrocarbon solvent, while removing alcohol as a by-product by azeotropic distillation in the presence of a polar solvent in a separating tank.

[9] The process for producing 3-oxopropionitrile compound as set forth in [5], [6], [7] or [8], wherein the alkali metal alkoxide is sodium methoxide or methanol solution thereof.

[10] The process for producing 3-oxopropionitrile compound as set forth in [5], [6], [7] or [8], wherein the aliphatic hydrocarbon is heptane.

[11] The process as set forth in [6] or [8], wherein the polar solvent is a mixed solvent of diethylene glycol monoethyl ether and diethylene glycol dimethyl ether, or 5-ethyl-2-picoline.

[12] A process for producing Z-3-acyloxyacrylonitrile compound characterized by isomerizing E-3-acyloxyacrylonitrile compound of formula (3) or a mixture thereof with Z-3-acyloxyacrylonitrile compound of formula (4) with an organic base such as amine or pyridine.

[13] The process as set forth in [1], [2], [3], [4], [5], [6], [7], [8], [9], [10], [11] or [12], wherein $Ar^1$ is phenyl group that may be substituted, thiazolyl group that may be substituted, pyrazolyl group that may be substituted, or triazolyl group that may be substituted.

[14] The process as set forth in [1], [2], [3], [4], [5], [6], [7], [8], [9], [10], [11], [12] or [13], wherein $Ar^2$ is pyrazolyl group that may be substituted, or thiazolyl group that may be substituted.

[15] The process as set forth in [1], [2], [3], [4], [5], [6], [7], [8], [9], [10], [11] or [12], wherein $Ar^1$ is 4-tert-butylphenyl group, and $Ar^2$ is 1,3,4-trimethyl-5-pyrazolyl group or 3-chloro-1,4-dimethyl-5-pyrazolyl group.

[16] The process as set forth in [1], [2], [3], [4], [5], [6], [7], [8], [9], [10], [11] or [12], wherein $Ar^1$ is 2-phenyl-5-ethyl-1,2,3-triazol-4-yl, and $Ar^2$ is 1,3,4-trimethyl-5-pyrazolyl group or 3-chloro-1,4-dimethyl-5-pyrazolyl group.

BEST MODE FOR CARRYING OUT THE INVENTION

The 3-oxopropionitrile compounds of formula (1), the acid chlorides of formula (2), the 3-acyloxyacrylonitrile compounds of formula (3) or (4), the acetonitrile compounds of formula (5), and the aromatic ester compounds of formula (6) in the present invention, $Ar^1$ and $Ar^2$ include phenyl group substituted with substituent A and heteroaryl group substituted with substituent A, substituent A includes substituent B that may be substituted, halogen atom, cyano group, nitro group and the like, substituent B includes alkyl group, haloalkyl group, phenyl group, heteroaryl group, alkoxy group and the like, $R^1$ includes alkyl group that may be substituted with substituent C, phenyl group that may be substituted with substituent D, or heteroaryl group that may be substituted with substituent D, substituent C includes alkoxy group, halogen atom, cyano group, nitro group and the like, substituent D includes alkyl group, alkoxy group, haloalkyl group, halogen atom, cyano group, nitro group and the like, $R^2$ includes alkyl group that may be substituted.

The heteroaryl group includes furan-2-yl group, furan-3-yl group, pyrrol-1-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, imidazol-1-yl group, imidazol-2-yl group, imidazol-4-yl group, isoxazol-3-yl group, isoxazol-4-yl group, isoxazol-5-yl group, isothiazol-3-yl group, isothiazol-4-yl group, isothiazol-5-yl group, pyrazol-1-yl group, pyrazol-3-yl group, pyrazol-4-yl group, pyrazol-5-yl group, 1,3,4-oxadiazol-2-yl group, 1,3,4-thiadiazol-2-yl group, 1,2,4-oxadiazol-3-yl group, 1,2,4-oxadiazol-5-yl group, 1,2,4-thiadiazol-3-yl group, 1,2,4-thiadiazol-4-yl group, 1,2,4-thiadiazol-5-yl group, 1,2,4-triazol-1-yl group, 1,2,4-triazol-3-yl group, 1,2,4-triazol-5-yl group, 1,2,3-triazol-4-yl group, 1,2,3-thiadiazol-5-yl group, 1,2,3-triazol-1-yl group, 1,2,3-triazol-2-yl group, 1,2,3,4-tetrazol-1-yl group, 1,2,3,4-tetrazol-2-yl group, 1,2,3,4-tetrazol-5-yl group, pyridin-2-yl group, pyridin-3-yl group, pyridin-4-yl group, pyrimidin-2-yl group, pyrimidin-4-yl group, pyrimidin-5-yl group, pyrazin-2-yl group, pyridazin-3-yl group, pyridazin-4-yl group, 1,3,5-triazin-2-yl group, 1,2,4-triazin-3-yl group, 1,2,4-triazin-5-yl group, 1,2,4-triazin-6-yl group, 1,2,4,5-tetrazin-3-yl group, 3-pyrazolin-1-yl group, 3-pyrazolin-3-yl group, 3-pyrazolin-4-yl group, 3-pyrazolin-5-yl group, 1-imidazolin-3-yl group, 1-imidazolin-2-yl group, 1-imidazolin-4-yl group, 4-imidazolin-2-yl group, 2-oxazolin-2-yl group, 2-oxazolin-4-yl group, 2-oxazolin-5-yl group, 2-isoxazolin-3-yl group, 2-isoxazolin-4-yl group, 2-isoxazolin-5-yl group, 2-thiazolin-2-yl group, 2-thiazolin-4-yl group, 3-thiazolin-2-yl group, imidazolidin-2-on-1-yl group, 2-imidazolinon-1-yl group, 3(2H)-pyridazinon-2-yl group, 3(2H)-pyridazinon-4-yl group, 3(2H)-pyridazinon-5-yl group or 3(2H)-pyridazinon-6-yl group, and the like, The alkyl group includes as straight-chain or branched alkyl group, methyl group, ethyl group, n-propyl group, isopropyl group, n-butyl group, isobutyl group, tert-butyl group, sec-butyl group, pentyl-1 group, pentyl-2 group, pentyl-3 group, 2-methylbutyl-1 group, 2-methylbutyl-2 group, 2-methylbutyl-3 group, 3-methylbutyl-1 group, 2,2-dimethylpropyl-1 group, hexyl-1 group, hexyl-2 group, hexyl-3 group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, n-heptyl group, n-octyl group, n-nonyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-icocyl group and the like.

The alkoxy group includes as straight-chain or branched alkoxy group, methoxy group, ethoxy group, n-propoxy group, isopropoxy group, n-butoxy group, isobutoxy group, sec-butoxy group, tert-butoxy group, n-pentyloxy group, 1-methylbutyloxy group, 2-methylbutyloxy group, 2-methylbutyloxy group, 1,1-dimethylpropyloxy group, 1,2-dimethylpropyloxy group, 2,2-dimethylpropyloxy group, 1-ethylpropyloxy group, n-hexyloxy group, 1-methylpentyloxy group, 2-methylpentyloxy group, 3-methylpentyloxy group, 4-methylpentyloxy group, 1,1-dimethylbutyloxy group, 1,2-dimethylbutyloxy group, 1,3-dimethylbutyloxy group, 2,2-dimethylbutyloxy group, 2,3-dimethylbutyloxy group, 3,3-dimethylbutyloxy group, 1-ethylbutyloxy group, 2-ethylbutyloxy group, 1,1,2-trimethylpropyloxy group, 1,2,2-trimethylpropyloxy group, 1-ethyl-1-methylpropyloxy group, 1-ethyl-2-methylpropyloxy group, n-heptyloxy group, n-octyloxy group, n-nonyloxy group and n-decyloxy group and the like.

The haloalkyl group includes as straight-chain or branched haloalkyl group, fluoromethyl group, chloromethyl group, bromomethyl group, fluoroethyl group, chloroethyl group, bromoethyl group, fluoro-n-propyl group, chloro-n-propyl group, difluoromethyl group, chlorodifluoromethyl group, trifluoromethyl group, dichloromethyl group, trichloromethyl group, difluoroethyl group, trifluoroethyl group, trichloroethyl group, chlorodifluoromethyl group, bromodifluoromethyl group, trifluorochloroethyl group, hexafluoro-n-propyl group, chlorobutyl group, fluorobutyl group, chloro-n-pentyl group, fluoro-n-pentyl group, chloro-n-hexyl group, fluoro-n-hexyl group and the like.

The halogen atom includes chlorine atom, fluorine atom, bromine atom, iodine atom.

The 3-oxopropionitrile compound is a tautomer of the 3-hydroxyacrylonitrile compound of formula (7)

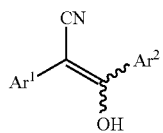

(7)

wherein $Ar^1$ and $Ar^2$ are have meaning similar to the above, respectively, and both are same compounds.

The reagents and reaction condition used in the reaction between 3-oxopropionitrile compound and acid chloride in order to obtain 3-acyloxyacrylonitrile compound are as follows, but the present invention is not limited thereto.

The method for removing hydrogen chloride as a by-product from the system without using a base during the reaction with the acid chloride is as follows, but the present invention is not limited thereto.

The used amount of the acid chloride is preferably 0.5 to 10 mol, more preferably 2 to 5 mol a 1 mol of 3-oxopropionitrile compound. In case where the acid chloride has a low boiling point, the excess one is recovered by distillation after the reaction and can be recycled.

The solvent used for the reaction is not specifically limited so long as it is an inert solvent for the present reaction, and for example includes ethers such as diethyl ether, methyl-tert-butyl ether, tetrahydrofuran, dimethoxymethane, diethoxymethane, ethylene glycol dimethyl ether, ethylene glycol diethyl ether, ethylene glycol dibutyl ether, diethylene glycol dimethyl ether, diethylene glycol diethyl ether, diethylene glycol dibutyl ether, triethylene glycol dimethyl ether, 1,4-dioxane and the like, aliphatic hydrocarbons such as pentane, hexane, cyclohexane, methylcyclohexane, heptane, octane, decane and the like, aromatic hydrocarbones such as benzene, toluene, o-xylene, m-xylene, p-xylene, ethylbenzene, chlorobenzene, o-dichlorobenzene, m-dichlorobenzene, p-dichlorobenzene, nitrobenzene, tetrahydronaphthalene and the like, nitriles such as acetonitrile, propionitrile and the like, esters such as methyl acetate, ethyl acetate, butyl acetate, ethyl propionate and the like. These solvents can be used singly or in a combination.

The used amount of the solvent is preferably 1 to 20 times, more preferably 3 to 10 times that of 3-oxopropionitrile compound.

The reaction temperature is preferably 50 to 120° C., more preferably 60 to 100° C.

The method for removing hydrogen chloride produced as a by-product during the reaction comprises adding dropwise an acid chloride while removing hydrogen chloride under a reduced pressure, or adding dropwise an acid chloride while removing hydrogen chloride together with or by release with a gas inert to the reaction, such as nitrogen, argon and the like the stream of which is flowed to the gas phase or the reaction solution and thereby exposed thereto. However, the present invention is not limited thereto.

If hydrogen chloride is not removed during the reaction, stereoselectivity is lowered and the reaction stops.

The time for adding dropwise the acid chloride is determined taking the removing rate of the hydrogen chloride gas as a by-product into account, and is a longer time than the time required for the removal thereof, and generally 1 to 15 hours. The reaction time after adding dropwise generally ranges from 1 hour to 10 hours.

At the conclusion of the reaction, excess acid chloride is recovered by distillation or decomposed with an alkaline solution after cooling below room temperature, and thereafter 3-acyloxyacrylonitrile compound can be obtained in a form of solution by extraction process. Further, crystals are separated out by cooling the solution as such, or crystals are obtained by distilling off the solvent, then adding crystallization solvent to be re-crystallized, and filtering.

The method of using the organic base or inorganic base when the acid chloride is reacted is as follows, but the present invention is not limited thereto.

The used amount of the acid chloride is preferably 0.5 to 2 mol, more preferably 1.0 to 1.2 mol a 1 mol of 3-oxopropionitrile compound.

The solvent used for the reaction is not specifically limited so long as it is an inert solvent for the present reaction, and for example includes ethers such as diethyl ether, methyl-tert-butyl ether, tetrahydrofuran, dimethoxymethane, diethoxymethane, ethylene glycol dimethyl ether, ethylene glycol diethyl ether, ethylene glycol dibutyl ether, diethylene glycol dimethyl ether, diethylene glycol diethyl ether, diethylene glycol dibutyl ether, triethylene glycol dimethyl ether, 1,4-dioxane and the like, aliphatic hydrocarbons such as pentane, hexane, cyclohexane, methylcyclohexane, heptane, octane, decane and the like, aromatic hydrocarbones such as benzene, toluene, o-xylene, m-xylene, p-xylene, ethylbenzene, chlorobenzene, o-dichlorobenzene, m-dichlorobenzene, p-dichlorobenzene, nitrobenzene, tetrahydronaphthalene and the like, nitriles such as acetonitrile, propionitrile and the like, esters such as methyl acetate, ethyl acetate, butyl acetate, ethyl propionate and the like. These solvents can be used singly or in a combination.

The used amount of the solvent is preferably 1 to 20 times, more preferably 3 to 10 times that of 3-oxopropionitrile compound.

The organic base includes tertiary amines such as trimethylamine, triethylamine, tripropylamine, tributylamine, N,N-dimethylaniline, N,N-dimethylbenzylamine and the like, pyridines such as pyridine, N,N-dimethylaminopyridine, picoline, lutidine, quinoline and the like, and organic bases that can be recovered and recycled, such as N,N-dimethylaniline, N,N-dimethylbenzylamine and the like are industrially preferable.

The used amount of the organic base is preferably 0.5 to 3 mol, more preferably 1.0 to 1.2 mol a 1 mol of 3-oxopropionitrile compound.

As the inorganic base, can be used compounds that are reacted with 3-oxopropionitrile compound to form a salt, and it includes hydrogen carbonates or carbonates of alkali metal, such as lithium carbonate, sodium hydrogen carbonate, sodium carbonate, potassium hydrogen carbonate, potassium carbonate, cesium carbonate and the like, carbonates of alkaline earth metal, such as magnesium carbonate and the like, hydroxides of alkali metal, such as lithium hydroxide, sodium hydroxide, potassium hydroxide and the like, hydroxides of alkaline earth metal, such as magnesium hydroxide, calcium hydroxide, barium hydroxide, strontium hydroxide and the like, and industrially inexpensive sodium carbonate, potassium carbonate, sodium hydroxide, potassium hydroxide and the like are preferable.

The used amount of the inorganic base is preferably 0.5 to 4.0 mol, more preferably 1.0 to 1.5 mol a 1 mol of 3-oxopropionitrile compound.

When the inorganic base is used, the used amount of the acid chloride can be reduced by reacting the base after producing a salt of 3-oxopropionitrile compound and then distilling out water formed as a by-product.

The reaction temperature in case where the organic base is used can range from an extremely-low temperature to a boiling point of the solvent, and preferably −10 to 20° C.

The reaction temperature in case where the inorganic base is used is required to be heated to a temperature from 50° C. to a boiling point of the solvent, more preferably a temperature from 60° C. to a boiling point of the solvent, when a salt of 3-oxopropionitrile compound is produced. The temperature in the reaction with the acid chloride after the salt formation can generally range from an extremely-low temperature to a boiling point of the solvent, and more preferably it is −10 to 20° C.

In case where the organic base or inorganic base is used, the process after the conclusion of the reaction comprises washing the reaction solution as such with water in case where the used solvent is insoluble in water, or removing the solvent by distillation in case where the solvent is soluble in water, or adding an extraction solvent to be extracted, and then obtaining 3-acyloxyacrylonitrile compound as a solution. Further, crystals are separated out by cooling the solution as such, or crystals are obtained by distilling off the solvent, then adding crystallization solvent to be re-crystallized, and filtering.

The regents and reaction condition used in the isomerization of E, Z mixture of 3-acyloxyacrylonitrile compounds in order to obtain Z-3-acyloxyacrylonitrile compound are as follows, but the present invention is not limited thereto.

The kind and used amount of the solvent, and the kind of the organic base are similar to those in the production of E-3-acyloxyacrylonitrile compound by using an organic base in the reaction with an acid chloride.

The used amount of the solvent varies depending on the kind thereof, but for example it is preferably 1 to 5 times that of 3-acyloxyacrylonitrile compound.

The used amount of the organic base is preferably 0.01 to 2.0 mol, preferably 0.1 to 1.0 mol a 1 mol of 3-acyloxypropionitrile compound.

The above-mentioned reaction comprises heating E, Z mixture of 3-acyloxyacrylonitrile compounds and an organic base in a solvent, then gradually cooling it while crystallizing Z-3-acyloxyacrylonitrile compound and filtering to obtain Z-3-acyloxyacrylonitrile compound. In this process, if a seed crystal of Z-3-acyloxyacrylonitrile compound is added during the cooling step, rapid crystallization and isomerization occur and thereby yield can be improved.

The regents and reaction condition used in the reaction of an acetonitrile compound and an aromatic ester compound in order to obtain 3-oxopropionitrile compound are as follows, but the present invention is not limited thereto.

The used amount of the acetonitrile compound is preferably 1.0 to 2.0 mol, more preferably 1.0 to 1.2 mol a 1 mol of the aromatic ester compound.

The ester moiety of the aromatic ester compound includes straight-chain or branched alkyl such as methyl, ethyl, propyl, isopropyl, butyl, pentyl and the like, substituted alkyl such as benzyl, phenethyl and the like. From a viewpoint of the ease of removal of the resulting alcohol, esters of low boiling point alcohol such as that of methyl, ethyl and the like are preferable, it is the most preferable methyl ester that alcohol formed as a by-product during the reaction is separated with an aliphatic hydrocarbon solvent.

The alkali metal alkoxide includes methoxide or ethoxide of lithium, sodium, potassium, rubidium, cesium and the like, etc. It is the most preferable sodium methoxide that alcohol formed as a by-product during the reaction is separated with a hydrocarbon solvent and that is inexpensive and industrially and universally used, and the methanol solution of sodium methoxide is further preferable from a viewpoint of ease of handling.

The used amount of the alkali metal alkoxide is preferably 0.5 to 2.0 mol, more preferably 1.0 to 1.3 mol a 1 mol of the aromatic ester compound.

The aliphatic hydrocarbon solvent includes 2-methylpentane, methylcyclopentane, hexane, cyclohexane, methylcyclohexane, heptane, octane, 2,2,4-trimethylpentane, nonane and the like. Cyclohexane, methylcyclohexane, heptane, octane, 2,2,4-trimethylpentane and the like are preferable as they are separated with methanol and have a relatively high boiling point. From viewpoints of cost and ease of handling, heptane is industrially more preferable. The hydrocarbon solvent can be used in a mixed solvent of two or more.

The used amount of the aliphatic hydrocarbon solvent is 3 to 20 times, more preferably 5 to 12 times that of the aromatic ester compound.

In addition, polar solvents can be optionally used. The polar solvent permits of rapidly separating out the alkali metal salt of 3-oxopropionitrile compound formed according to the reaction as crystal. When the alkali metal salt is separated out as oily product in case where only an aliphatic hydrocarbon solvent is used, it is often adhered to the tank wall and crystallized. Therefore, it is often useful to make an polar solvent present.

The polar solvent includes high boiling point solvents, for example, pyridines such as 2-picoline, 3-picoline, 4-picoline, 5-ethyl-2-picoline, 2,3-lutidine, 2,4-lutidine, 3,5-lutidine, 2,6-lutidine, 2,4,6-trimethylpyridine, quinoline and the like, ethers such as dibutyl ether, diethylene glycol dimethyl ether, diethylene glycol diethyl ether, diethylene glycol dibutyl ether, triethylene glycol dimethyl ether, triethylene glycol diethyl ether and the like, alcohols having ether structure, such as diethylene glycol monomethyl ether, diethylene glycol monoethyl ether, diethylene glycol monobutyl ether, triethylene glycol monomethyl ether, triethylene glycol monoethyl ether and the like. Among them, 5-ethyl-2-picoline, diethylene glycol dimethyl ether, diethylene glycol monoethyl ether and the like are preferable as they are solvents that can be separated and removed in waste water in the post-treatment. These solvents can be used in a mixed state.

The used amount of the polar solvent is preferably 0.01 to 5 times, more preferably 0.1 to 1 time that of the aromatic ester compound.

Further, solvents that do not affect the reaction, such as aromatics, ethers, alcohols and the like can be mixed with the above-mentioned solvent in a small amount so long as the former does not inhibit separation between the hydrocarbon solvent and methanol.

The reaction is carried out by gradually adding sodium methoxide while refluxing a mixture of the acetonitrile compound, aromatic ester compound, hydrocarbon solvent and polar solvent through a separating tank. In this process, methanol formed as a by-product is removed by separating into phases in the separating tank.

The reaction temperature ranges from room temperature to a boiling point of the used solution, and preferably from 60° C. to a boiling point of the reaction solvent. The higher the temperature is, the higher the reaction rate is.

The reaction pressure is normal pressure or a reduced pressure. The reflux in a state of a reduced pressure is preferable from a viewpoint of ease of controlling the reaction temperature.

The addition of sodium methoxide is carried out at a rate that is the same as or lower than that of separation of methanol in a separating tank. The time of adding dropwise is generally 1 to 15 hours. The reaction time after adding dropwise generally ranges from 1 hour to 15 hours.

In order to promote a smooth reaction thereby improving further yield, the reflux by use of a rectification column can be carried out. The rectification column makes possible to improve separation efficiency of methanol and at the same time to prevent distilling off acetonitrile compound and aromatic ester compound as starting materials.

In addition, when water in the starting materials is removed by azeotropic dehydration prior to the addition of sodium methoxide, hydrolysis of the aromatic ester compound is inhibited and thereby the yield is improved.

In presence of oxygen in the reaction, the reaction solution turns black, a lowering of yield occurs, and an increase in insoluble products occurs when the solution is separated into phases in the post-treatment. Therefore, the reaction is required to be carried out in an inert gas atmosphere such as nitrogen.

In the process after the completion of the reaction, the reaction solution is cooled to 30° C. or less, water is added to be separated into the hydrocarbon solvent phase and an aqueous phase containing alkali metal salts of 3-oxopropionitrile compound. The separation step permits transfer of most of acetonitrile compound and aromatic ester compound as the reminder of starting materials and lipid-soluble by-products to the hydrocarbon solvent phase and removal thereof. For further purification, the aqueous phase containing alkali metal salts of 3-oxopropionitrile compound can be washed with a small amount of hydrocarbon solvent and separated into phases. 3-oxopropionitrile compound can be obtained as crystal by neutralizing the aqueous phase with hydrochloric acid, acetic acid and the like, or as solution by making an extraction solvent such as toluene, xylene and the like present when the neutralization is carried out.

EXAMPLES

Hereinafter, the present invention is further described according to examples to which the present invention is not limited.

Example 1

In a 10 L-reaction flask, 456 g (1.47 mol) of 3-oxo-2-(4-tert-butylphenyl)-3-(1,3,4-trimethylpyrazol-5-yl) propionitrile and 2738 g of xylene were added, the temperature was raised to 70° C., and 534 g (4.43 mol) of pivaloyl chloride was added dropwise under reflux over 10 hours while removing hydrogen chloride under a reduced pressure at 68 to 71° C./10 to 13 kPa. After reacting as such for 3 hours, 2181 g of a mixture of pivaloyl chloride and xylene was distilled off at 70° C. under a reduced pressure in order to remove excess pivaloyl chloride. After adding 456 g of warm water of 70° C., 228 g of 2.7% sodium hydrogen carbonate aqueous solution was added dropwise. After separating the resulting aqueous phase, the resulting organic phase was washed with 456 g of warm water of 70° C., the resulting aqueous phase was separated to obtain a xylene solution. A quantitative analysis with liquid chromatography showed that the xylene solution contained 555 g (yield 95.6%) of (2E)-3-(2,2-dimethylpropanoyloxy)-2-(4-tert-butylphenyl)-3-(1,3,4-trimethylpyrazol-5-yl) acrylonitrile. After distilling off xylene at 90° C., 1141 g of heptane was added, and crystallization was carried out by gradually cooling from 70° C. After aging at 0° C. for 1 hour, the resulting crystal was filtered, and dried to obtain 533 g (yield 91.9%) of (2E)-3-(2,2-dimethylpropanoyloxy)-2-(4-tert-butylphenyl)-3-(1,3,4-trimethylpyrazol-5-yl) acrylonitrile (melting point: 110° C.).

Example 2

In a 2 L-reaction flask equipped with a rectification column, 116.7 g (0.55 mol) of 2-phenyl-4-cyanomethyl-5-ethyl-1,2,3-triazole, 91 g (0.5 mol) of 1,3,4-trimethylpyrazol-5-carboxylic acid ethyl ester, 900 g of heptane, 60 g of diethylene glycol dimethyl ether, and 30 g of diethylene glycol monoethyl ether were added, then azeotropic dehydration was carried out by heating at 90 to 95° C., thereafter 115.5 g (0.6 mol) of 28% sodium was added dropwise over 10 hours, and the resulting mixture was reacted for 7 hours. After cooling to 30° C. or less, 3000 g of water was added to separate out heptane phase, and further the aqueous phase was washed with 600 g of heptane, the heptane phase was separated out, 900 g of xylene was added, then 62.5 g (0.6 mol) of 35% hydrochloric acid was added dropwise to be neutralized. The aqueous phase was separated out, washed with 600 g of water two times, the aqueous phase was separated out to obtain a xylene solution containing 156.8 g (yield 90%) of 3-oxo-2-(2-phenyl-5-ethyl-1,2,3-triazol-4-yl)-3-(1,3,4-trimethylpyrazol-5-yl) propionitrile.

Example 3

In a 10 L-reaction flask, 594 g (1.92 mol) of 3-oxo-2-(4-tert-butylphenyl)-3-(1,3,4-trimethylpyrazol-5-yl) propionitrile and 6000 g of tetrahydrofuran were added, 214 g (2.11 mol) of triethyl amine was added and then 255 g (2.11 mol) of pivaloyl chloride was added dropwise at 25 to 27° C. over 1 hour. After reacting for 20 hours, tetrahydrofuran was removed by concentrating under a reduced pressure, and then 1800 g of toluene and 1800 g of water were added to separate out toluene phase. After distilling out toluene, 794 g of hexane was added and dissolved, and crystallization was carried out by gradually cooling to 7° C. After filtering, the crystal was washed with 1000 g of hexane cooled at 5° C., dried to obtain 554 g (yield 73.4%) of (2E)-3-(2,2-dimethylpropanoyloxy)-2-(4-tert-butylphenyl)-3-(1,3,4-trimethylpyrazol-5-yl) acrylonitrile.

Example 4

In a 10 L-reaction flask, 223 g (0.639 mol) of 3-oxo-2-(4-tert-butylphenyl)-3-(1,3,4-trimethylpyrazol-5-yl) propionitrile and 4456 g of 1,4-doxane were added, 97.2 g (0.351 mol) of potassium carbonate was added thereto, then the temperature was raised to 60° C., and the resulting mixture was stirred for 3 hours. In order to remove water formed as a by-product, 486 g of the solvent was distilled off under a reduced pressure, then 92.5 g (0.767 mol) of pivaloyl chloride was dropwise at 60° C. over 1 hour. After reacting for 2 hours, 1,4-dioxane being a solvent was distilled off, then 456 g of toluene was added and dissolved. The resulting solution was washed two times with 446 g of water to obtain a toluene solution containing 217 g (yield 78.6%) of (2Z)-3-(2,2-dimethylpropanoyloxy)-2-(5-ethyl-2-phenyl-1,2,3-triazol-4-yl)-3-(1,3,4-trimethylpyrazol-5-yl)acrylonitrile and 43 g (yield 15.5%) of (2E)-3-(2,2-dimethylpropanoyloxy)-2-(5-ethyl-2-phenyl-1,2,3-triazol-4-yl)-3-(1,3,4-trimethylpyrazol-5-yl)acrylonitrile. After distilling off toluene under a reduced pressure, the residue was dissolved in 780 g of acetonitrile, and crystallization was carried out by gradually cooling to 0° C. After filtering, the resulting crystal was washed with 260 g of acetonitrile, then dried to obtain 166 g (yield 63.1%) of (2Z)-3-(2,2-dimethylpropanoyloxy)-2-(5-ethyl-2-phenyl-1,2,3-triazol-4-yl)-3-(1,3,4-trimethylpyrazol-5-yl)acrylonitrile.

Example 5

In 400 ml of acetonitrile, a mixture of 180 g of (2E)-3-(2,2-dimethylpropanoyloxy)-2-(4-tert-butyl phenyl)-3-(1,3,4-trimethylpyrazol-5-yl) acrylonitrile and 20 g of pyridine was stirred under a reflux condition for 72 hours. An analysis with liquid chromatography showed that the ratio of (2E)-3-(2,2-dimethylpropanoyloxy)-2-(4-tert-butylphenyl)-3-(1,3,4-trimethylpyrazol-5-yl) acrylonitrile and (2Z)-3-(2,2-dimethylpropanoyloxy)-2-(4-tert-butyl phenyl)-3-(1,3,4-trimethylpyrazol-5-yl) acrylonitrile was 5:6. Then, the temperature was dropped by 10° C. a 1 hour, and finally the mixture was stirred at 15° C. for 24 hours. To the homogeneous solution, a seed crystal of (2Z)-3-(2,2-dimethylpropanoyloxy)-2-(4-tert-butylphenyl)-3-(1,3,4-trimethylpyrazol-5-yl) acrylonitrile was added, stirred for 3 hours, and then cooled, and the liquid temperature after 1 hour was adjusted to 5° C. After stirring at 5° C. for 1 hour, the solution was filtered and the resulting crystal was washed with 150 ml of heptane of 5° C., and dried to obtain 82 g of (2Z)-3-(2,2-dimethylpropanoyloxy)-2-(4-tert-butylphenyl)-3-(1,3,4-trimethylpyrazol-5-yl) acrylonitrile (melting point: 146° C.) having a purity of 99%.

Example 6

In a 3 L-reaction flask, 156.8 g (0.45 mol) of 3-oxo-2-(2-phenyl-5-ethyl-1,2,3-triazol-4-yl)-3-(1,3,4-trimethylpyrazol-5-yl) propionitrile and 900 g of xylene were added, the temperature was raised to 70° C., and 162.7 g (1.35 mol) of pivaloyl chloride was added dropwise under reflux over 10 hours while removing hydrogen chloride under a reduced pressure at 68 to 71° C./10 to 13 kPa. After reacting as such for 5 hours, 740 g of a mixture of pivaloyl chloride and xylene was distilled off at 70° C. under a reduced pressure in order to remove excess pivaloyl chloride. After adding 156 g of warm water of 70° C., 70 g of 2.7% sodium hydrogen carbonate aqueous solution was added dropwise. After separating the resulting aqueous phase, the resulting organic phase was washed with 156 g of warm water of 70° C., the resulting aqueous phase was separated to obtain a xylene solution containing 181 g (yield 93.0%) of (2E)-3-(2,2-dimethylpropanoyloxy)-2-(2-phenyl-5-ethyl-1,2,3-triazol-4-yl)-3-(1,3,4-trimethylpyrazol-5-yl)acrylonitrile. After distilling off most of xylene at 90° C. under a reduced pressure, 540 g of acetonitrile was added, and crystallization was carried out by gradually cooling from 70° C. After stirring at 0° C. for 1 hour, the resulting crystal was filtered, and dried to obtain 163.5 g (yield 84%) of (2E)-3-(2,2-dimethylpropanoyloxy)-2-(2-phenyl-5-ethyl-1,2,3-triazol-4-yl)-3-(1,3,4-trimethylpyrazol-5-yl)acrylonitrile (melting point: 119° C.).

Example 7

In 600 g of acetonitrile, a mixture of 216.3 g of (2E)-3-(2,2-dimethylpropanoyloxy)-2-(2-phenyl-5-ethyl-1,2,3-triazol-4-yl)-3-(1,3,4-trimethylpyrazol-5-yl)acrylonitrile and 20 g of pyridine was stirred under a reflux condition for 5 hours. An analysis with liquid chromatography showed that the ratio of (2Z)-3-(2,2-dimethylpropanoyloxy)-2-(2-phenyl-5-ethyl-1,2,3-triazol-4-yl)-3-(1,3,4-trimethylpyrazol-5-yl)acrylonitrile and (2E)-3-(2,2-dimethylpropanoyloxy)-2-(2-phenyl-5-ethyl-1,2,3-triazol-4-yl)-3-(1,3,4-trimethylpyrazol-5-yl) acrylonitrile in the homogeneous reaction solution was about 4:6. Then, the solution was gradually cooled and adjusted to 25° C. after 20 hours. Thereafter, the slurry solution obtained by stirring at 25° C. for 48 hours was cooled to 10° C. After 30 minutes, the solution was filtered, the resulting crystal was washed with 150 ml of 1:1 solution of acetonitrile:heptane of 5° C., and dried to obtain 166 g of (2Z)-3-(2,2-dimethylpropanoyloxy)-2-(2-phenyl-5-ethyl-1,2,3-triazol-4-yl)-3-(1,3,4-trimethylpyrazol-5-yl)acrylonitrile (melting point: 143° C.) having a purity of 99%.

Example 8

In a 300 mL-reaction flask equipped with a rectification column and a separating tank, 11.3 g (65.2 mmol) of 4-tert-butylphenylacetonitrile, 10.8 g (59.5 mmol) of 1,3,4-trimethylpyrazol-5-carboxylic acid ethyl ester, 100 g of heptane, 10.0 g of 5-ethyl-2-picoline were added, the atmosphere was substituted with nitrogen, then azeotropic dehydration was carried out by heating at 90 to 95° C. for 1 hour. The temperature was maintained, 13.8 g (71.5 mmol) of 28% sodium methoxide methanol solution was added dropwise over 3 hours, and the resulting mixture was further reacted for 11 hours. After cooling to 30° C. or less, 108 g of water was added to separate out heptane phase and obtain an aqueous phase. A quantitative analysis of the obtained aqueous phase with liquid chromatography showed that the aqueous phase contained 15.5 g (yield 84.5%) of 3-oxo-2-(4-tert-butylphenyl)-3-(1,3,4-trimethylpyrazol-5-yl) propionitrile.

Example 9

In a 300 mL-reaction flask equipped with a rectification column and a separating tank, 11.3 g (65.2 mmol) of 4-tert-butylphenylacetonitrile, 10.8 g (59.5 mmol) of 1,3,4-trimethylpyrazol-5-carboxylic acid ethyl ester, 100 g of heptane, 10.0 g of 5-ethyl-2-picoline, and 3.0 g of diethylene glycol monoethyl ether were added, the atmosphere was substituted with nitrogen, then azeotropic dehydration was carried out by heating at 90 to 95° C. for 1 hour. The temperature was maintained, 13.8 g (71.5 mmol) of 28% sodium methoxide methanol solution was added dropwise over 5 hours, and the resulting mixture was further reacted for 5 hours. After cooling to 30° C. or less, 108 g of water was added to separate out heptane phase and obtain an aqueous phase. A quantitative analysis of the obtained aqueous phase with liquid chromatography showed that the aqueous phase contained 17.0 g (yield 92.1%) of 3-oxo-2-(4-tert-butylphenyl)-3-(1,3,4-trimethylpyrazol-5-yl) propionitrile.

Example 10

In a 300 mL-reaction flask equipped with a rectification column and a separating tank, 11.3 g (65.2 mmol) of 4-tert-butylphenylacetonitrile, 10.8 g (59.5 mmol) of 1,3,4-trimethylpyrazol-5-carboxylic acid ethyl ester, 100 g of heptane, and 1.5 g of diethylene glycol monoethyl ether were added, the atmosphere was substituted with nitrogen, then azeotropic dehydration was carried out by heating at 90 to 95° C. for 1 hour. The temperature was maintained, 13.8 g (71.5 mmol) of 28% sodium methoxide methanol solution was added dropwise over 3 hours, and the resulting mixture was further reacted for 7 hours. After cooling to 30° C. or less, 108 g of water was added to separate out heptane phase and obtain an aqueous phase. A quantitative analysis of the obtained aqueous phase with liquid chromatography showed that the aqueous phase contained 15.7 g (yield 85.8%) of 3-oxo-2-(4-tert-butylphenyl)-3-(1,3,4-trimethylpyrazol-5-yl) propionitrile.

Example 11

In a 10 L-reaction flask equipped with a rectification column and a separating tank, 314 g (1.81 mol) of 4-tert-butylphenylacetonitrile, 300 g (1.65 mol) of 1,3,4-trimethylpyrazol-5-carboxylic acid ethyl ester, 3000 g of heptane, 225 g of diethylene glycol dimethyl ether, and 99 g of diethylene glycol monoethyl ether were added, the atmosphere was substituted with nitrogen, then azeotropic dehydration was carried out by heating at 90 to 95° C. for 1 hour. The temperature was maintained, 381 g (1.98 mol) of 28% sodium methoxide methanol solution was added dropwise over 10 hours, and the resulting mixture was further reacted for 7 hours. After cooling to 30° C. or less, 3000 g of water was added to separate out heptane phase, and the resulting aqueous phase was further washed with 600 g of heptane to separate out heptane phase. A quantitative analysis of the obtained aqueous phase with liquid chromatography showed that the aqueous phase contained 466 g (yield 91.5%) of 2-(4-tert-butylphenyl)-3-(1,3,4-trimethyl-5-pyrazolyl)-3-oxopropionitrile. After adding 2760 g of xylene to the aqueous phase, 206 g (1.98 mol) of 35% hydrochloric acid was added dropwise to be neutralized. After separating out the aqueous phase, the resulting organic phase was washed two times with 600 g of water and the aqueous phase was separated out to obtain xylene solution of 3-oxo-2-(4-tert-butylphenyl)-3-(1,3,4-trimethylpyrazol-5-yl) propionitrile. A quantitative analysis with liquid chromatography showed that the xylene solution contained 456 g (yield 89.6%) of 3-oxo-2-(4-tert-butylphenyl)-3-(1,3,4-trimethylpyrazol-5-yl) propionitrile.

Example 12

In a 2000 ml-reaction flask equipped with a rectification column and a separating tank, 83.7 g (483 mmol) of 4-tert-butylphenylacetonitrile, 80.0 g (439 mmol) of 1,3,4-trimethylpyrazol-5-carboxylic acid ethyl ester, 640 g of heptane, and 160 g of diethylene glycol monobutyl ether were added, the atmosphere was substituted with nitrogen, then azeotropic dehydration was carried out by heating at 90 to 95° C. for 1 hour. The temperature was maintained, 93.2 g (482 mmol) of 28% sodium methoxide methanol solution was added dropwise over 3 hours, and the resulting mixture was further reacted for 10 hours. After cooling to 30° C. or less, 600 g of water was added to separate out heptane phase, and the resulting aqueous phase was washed with 160 g of heptane and 400 g of toluene was added, then pH was adjusted to 7 with 35% hydrochloric acid. After separating into phases, the toluene phase was washed two times with 160 g of water to obtain a toluene solution containing 116 g (yield 85.1%) of 3-oxo-2-(4-tert-butylphenyl)-3-(1,3,4-trimethylpyrazol-5-yl) propionitrile. Toluene was distilled off under a reduced pressure, then 120 g of di-n-butyl ether was added and completely dissolved therein at a temperature of 120° C. Thereafter, the solution was cooled to 20° C., the resulting crystal was further dispersed in 150 g of di-n-butylether, 200 g of n-hexane was added therein and stirred at 10° C. for 1 hour. The resulting crystal was filtered and washed with 150 g of n-hexane to obtain 92.3 g of 3-oxo-2-(4-tert-butyl phenyl)-3-(1,3,4-trimethylpyrazol-5-yl) propionitrile (melting point 178° C.).

Example 13

In a 2 L-reaction flask equipped with a rectification column, 106 g (0.5 mol) of 2-phenyl-4-cyanomethyl-5-ethyl-1,2,3-triazole, 91 g (0.5 mol) of 1,3,4-trimethylpyrazol-5-carboxylic acid ethyl ester, 530 g of heptane, and 106 g of diethylene glycol dimethyl ether were added, then azeotropic dehydration was carried out by heating at 90 to 95° C. Thereafter 61.7 g (0.55 mol) of potassium-tert-butoxide was carefully added under nitrogen atmosphere, then the resulting solution was heated at 95° C. and reacted for 15 hours while removing the eluent from the rectification column. After cooling to 30° C. or less, 3000 g of water was added to separate out heptane phase, and the resulting aqueous phase was further washed with 600 g of heptane to separate into phases. A quantitative analysis of the obtained aqueous phase with liquid chromatography showed that the aqueous phase contained 118.5 g (yield 68%) of 2-(2-phenyl-5-ethyl-1,2,3-triazol-4-yl)-3-(1,3,4-trimethyl-5-pyrazolyl)-3-oxopropionitrile. The aqueous solution was warmed at 40° C., pH was adjusted to 1 by adding 35% hydrochloric acid with stirring. The crystal obtained by cooling to 15° C. over 2 hours was filtered. The crystal cake was washed three times with 200 ml of water and then dried to obtain 116 g (yield 66.5%) of 2-(2-phenyl-5-ethyl-1,2,3-triazol-4-yl)-3-(1,3,4-trimethyl-5-pyrazolyl)-3-oxopropionitrile (melting point 119° C.).

Example 14

In a 10 L-reaction flask equipped with a rectification column and a separating tank, 314 g (1.81 mol) of 4-tert-butylphenylacetonitrile, 300 g (1.65 mol) of 1,3,4-trimethylpyrazol-5-carboxylic acid ethyl ester, 3000 g of heptane, 225 g of diethylene glycol dimethyl ether, and 99 g of diethylene glycol monoethyl ether were added, the atmosphere was substituted with nitrogen, then azeotropic dehydration was carried out by heating at 90 to 95° C. for 1 hour. The temperature was maintained, 381 g (1.98 mol) of 28% sodium methoxide methanol solution was added dropwise over 10 hours, and the resulting mixture was further reacted for 10 hours. During this reaction, it is continued to remove alcohol separated in the phase under the heptane phase in the separating tank. After cooling to 30° C. or less, 3000 g of water was added to separate out heptane phase, and the resulting aqueous phase was washed with 600 g of heptane to separate out heptane phase. A quantitative analysis of the obtained aqueous phase with liquid chromatography showed that the aqueous phase contained 478 g (yield 94.0%) of 2-(4-tert-butylphenyl)-3-(1,3,4-trimethyl-5-pyrazolyl)-3-oxopropionitrile. To the aqueous phase, 206 g (1.98 mol) of 35% hydrochloric acid was gradually added dropwise to be neutralized. After stirring for 1 hour, separated crystal was filtered, washed with 300 g of water, and then dried to obtain 469 g (yield 92.0%) of 3-oxo-2-(4-tert-butyl phenyl)-3-(1,3,4-trimethylpyrazol-5-yl) propionitrile.

Example 15

In a 10 L-reaction flask equipped with a rectification column and a separating tank, 314 g (1.81 mol) of 4-tert-butylphenylacetonitrile, 274 g (1.65 mol) of 1,3,4-trimethylpyrazol-5-carboxylic acid methyl ester, 3000 g of heptane, 225 g of diethylene-glycol dimethyl ether, and 99 g of diethylene glycol monoethyl ether were added, the atmosphere was substituted with nitrogen, then azeotropic dehydration was carried out by heating at 90 to 95° C. for 1 hour. The temperature was maintained, 381 g (1.98 mol) of 28% sodium methoxide methanol solution was added dropwise over 13 hours, and the resulting mixture was further reacted for 10 hours. During this reaction, it is continued to remove alcohol separated in the phase under the heptane phase in the separating tank. After cooling to 30° C. or less, 3000 g of water was added to separate out heptane phase, and the resulting aqueous phase was further washed with 600 g of heptane to separate out heptane phase. A quantitative analysis of the obtained aqueous phase with liquid chromatography showed that the aqueous phase contained 486 g (yield 95.5%) of 2-(4-tert-butylphenyl)-3-(1,3,4-trimethyl-5-pyrazolyl)-3-oxopropionitrile. To the aqueous phase, 206 g (1.98 mol) of 35% hydrochloric acid was gradually added dropwise to be neutralized. After stirring for 1 hour, separated crystal was filtered, washed with 300 g of water, and then dried to obtain 475 g (yield 93.4%) of 3-oxo-2-(4-tert-butylphenyl)-3-(1,3,4-trimethylpyrazol-5-yl) propionitrile.

EFFECT OF THE INVENTION

According to the present invention, acrylonitrile compounds can be produced in a high yield and selective manner.

The invention claimed is:

1. A process for producing Z-3-acyloxyacrylonitrile compound

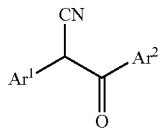

(1)

comprising isomerizing E-3-acyloxyacrylonitrile compound of formula (3)

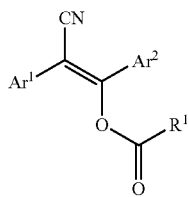

(3)

wherein $Ar^1$ and $Ar^2$ are independently of each other an aromatic substituent that may be substituted, and $R^1$ is an alkyl group that may be substituted, or an aromatic substituent that may be substituted, with an organic base; or isomerizing a mixture of the compound of formula (3) and Z-3-acyloxyacrylonitrile compound of formula (4)

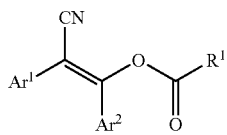

(4)

wherein $Ar^1$, $Ar^2$ and $R^1$ have a meaning similar to the above, with an organic base.

2. The process according to claim 1, wherein the organic base is an amine.

3. The process according to claim 1, wherein the organic base is pyridine.

4. The process according to claim 1, wherein isomerizing E-3-acyloxyacrylonitrile compound of formula (3) with the organic base occurs in a solvent; or isomerizing a mixture of the compound of formula (3) and Z-3-acyloxyacrylonitrile compound of formula (4) with the organic base occurs in a solvent.

5. The process according to claim 1, wherein isomerizing E-3-acyloxyacrylonitrile compound of formula (3) with the organic base occurs in a solvent at a temperature in the range of from 10° C. to a refluxing temperature of the solvent; or isomerizing a mixture of the compound of formula (3) and Z-3-acyloxyacrylonitrile compound of formula (4) with the organic base occurs in a solvent at a temperature in the range of from 10° C. to a refluxing temperature of the solvent.

6. The process according to claim 5, wherein the temperature during isomerization reaches the solvent's refluxing temperature.

7. The process according to claim 6, further comprising a cooling step in which the temperature is adjusted from the refluxing temperature of the solvent to 15° C. or less.

8. The process according to claim 7, further comprising adding a seed crystal of the Z-3-acyloxyacrylonitrile compound after the temperature as been reduced to 15° C. or less.

9. The process according to claim 1, wherein isomerizing E-3-acyloxyacrylonitrile compound of formula (3) with the organic base occurs in a solvent at a temperature in the range of from 5° C. to a refluxing temperature of the solvent; or isomerizing a mixture of the compound of formula (3) and Z-3-acyloxyacrylonitrile compound of formula (4) with the organic base occurs in a solvent at a temperature in the range of from 5° C. to a refluxing temperature of the solvent.

10. The process according to claim 9, wherein the temperature during isomerization reaches the solvent's refluxing temperature.

11. The process according to claim 10, further comprising a cooling step in which the temperature is adjusted from the refluxing temperature of the solvent to 15° C. or less.

12. The process according to claim 11, further comprising adding a seed crystal of the Z-3-acyloxyacrylonitrile compound after the temperature as been reduced to 15° C. or less.

* * * * *